(12) United States Patent
Yan et al.

(10) Patent No.: US 10,682,255 B2
(45) Date of Patent: Jun. 16, 2020

(54) ULTRASONIC NEEDLE AND APPARATUS APPLIED FOR VITRECTOMY

(71) Applicant: INNOLCON MEDICAL TECHNOLOGY (SUZHOU) CO. LTD, Suzhou (CN)

(72) Inventors: Zhongyu Yan, Suzhou (CN); Wei Luo, Suzhou (CN)

(73) Assignee: Innolcon Medical Technology (Suzhou) Co. Ltd, Suzhou (CN)

( * ) Notice: Subject to any disclaimer, the term of this patent is extended or adjusted under 35 U.S.C. 154(b) by 216 days.

(21) Appl. No.: 15/573,810

(22) PCT Filed: Apr. 28, 2016

(86) PCT No.: PCT/CN2016/080452
§ 371 (c)(1),
(2) Date: Nov. 13, 2017

(87) PCT Pub. No.: WO2016/184300
PCT Pub. Date: Nov. 24, 2016

(65) Prior Publication Data
US 2018/0256396 A1    Sep. 13, 2018

(30) Foreign Application Priority Data
May 15, 2015   (CN) .......................... 2015 1 0249346

(51) Int. Cl.
*A61F 9/007* (2006.01)
*A61B 17/22* (2006.01)
(Continued)

(52) U.S. Cl.
CPC .... *A61F 9/00745* (2013.01); *A61B 17/22004* (2013.01); *A61B 17/22012* (2013.01);
(Continued)

(58) Field of Classification Search
CPC ......... Y10T 29/49925; Y10T 29/49927; Y10T 29/49929; A61B 17/22004–22029; A61B 2017/00477–00486
See application file for complete search history.

(56) References Cited

U.S. PATENT DOCUMENTS 5,222,937 A    6/1993   Kagawa
5,651,783 A    7/1997   Reynard
(Continued)

FOREIGN PATENT DOCUMENTS

CN    102256574 A    11/2011
CN    104055620 A    9/2014
(Continued)

*Primary Examiner* — Nathan R Price
*Assistant Examiner* — Anh Bui
(74) *Attorney, Agent, or Firm* — Seed Intellectual Property Law Group LLP

(57) ABSTRACT

This disclosure disclosed an ultrasonic needle and apparatus used for removal of the vitreous body and other tissues. An ultrasonic vitrectomy needle, comprising: a connector, a connected inner needle, and an outer sheath. The length of the outer sheath at the distal end is slightly longer than that of the inner needle; the sheath distal end is of blind with smooth surface, but there is an open cut at the side of the distal end used for aspirating the vitreous body. The benefits of this disclosure: due to the difficulty if not impossible in the prior arts making a slim long center bore needle for ultrasonic surgical system, this disclosure clears the way to make the ultrasonic vitrectomy a practical reality; the ultrasonic vibration inherent advantages of the quietness, minuscule displacement, liquid repulsion and viscosity reduction improve safety of the surgery; the possibility of integrating ultrasonic vitrectomy and ultrasonic phaco emulsification procedures simplifies the complexity from prior arts, thus brings ease to the ophthalmic surgeries and reduces the cost.

10 Claims, 3 Drawing Sheets

(51) Int. Cl.
*A61B 17/00* (2006.01)
*A61M 1/00* (2006.01)

(52) U.S. Cl.
CPC ..... *A61B 17/2202* (2013.01); *A61B 17/22022* (2013.01); *A61B 17/22029* (2013.01); *A61B 2017/00477* (2013.01); *A61B 2017/00482* (2013.01); *A61B 2017/00486* (2013.01); *A61B 2017/22005* (2013.01); *A61B 2017/22007* (2013.01); *A61B 2017/22008* (2013.01); *A61B 2017/22009* (2013.01); *A61B 2017/22011* (2013.01); *A61B 2017/22014* (2013.01); *A61B 2017/22015* (2013.01); *A61B 2017/22017* (2013.01); *A61B 2017/22018* (2013.01); *A61B 2017/22021* (2013.01); *A61B 2017/22024* (2013.01); *A61B 2017/22025* (2013.01); *A61B 2017/22027* (2013.01); *A61B 2017/22028* (2013.01); *A61M 1/008* (2013.01)

(56) References Cited

U.S. PATENT DOCUMENTS

| | | |
|---|---|---|
| 5,667,489 A | 9/1997 | Kraff et al. |
| 5,746,713 A | 5/1998 | Hood et al. |
| 5,935,096 A | 8/1999 | Barrett |
| 5,989,208 A * | 11/1999 | Nita ............ A61B 17/22 604/22 |
| 6,270,471 B1 * | 8/2001 | Hechel ............ A61B 17/22012 604/22 |
| 8,439,938 B2 | 5/2013 | Moore, Jr. |
| 2010/0160852 A1 | 6/2010 | Moore, Jr. |
| 2012/0221009 A1 | 8/2012 | Tada et al. |
| 2012/0316490 A1 | 12/2012 | Perkins |
| 2014/0074011 A1 | 3/2014 | Charles |
| 2014/0074013 A1 | 3/2014 | McCary et al. |
| 2015/0196426 A1 | 7/2015 | Kuebler et al. |

FOREIGN PATENT DOCUMENTS

| | | |
|---|---|---|
| CN | 104055622 A | 9/2014 |
| CN | 203988621 U | 12/2014 |
| CN | 204072457 U | 1/2015 |
| CN | 204072458 U | 1/2015 |
| CN | 204734603 U | 11/2015 |
| CN | 105310821 A | 2/2016 |
| EP | 2712591 A1 | 4/2014 |
| WO | 2014048550 A1 | 4/2014 |

* cited by examiner

ULTRASONIC NEEDLE AND APPARATUS APPLIED FOR VITRECTOMY

BACKGROUND

Technical Field

This invention is related to medical device and the related method, particularly to the ultrasonic vitrectomy and its needle.

Description of the Related Art

Human eyes working principle is like this: a light beam passing through the cornea and lens to focus, then passing through the vitreous body and falling on the retina to form an image. The focusing quality is affected by many factors, including the size and shape of the eye and the transparency of the cornea, lens and vitreous body.

Vitreous body is a transparent tissue located at the posterior chamber of the eye. When an eye has a disease, such as hemorrhage, retina tear, sometimes need to take out the vitreous body which is called vitrectomy. Commonly used vitrectomy devices include vitrectomy hand piece, illuminating tube and irrigation needle etc. In prior arts, the commonly used vitrectomy equipment is driven by pneumatic source, and occasionally by electrical source; these complex apparatus require specified driven source. For the often used ophthalmic surgical equipment, the vitrectomy apparatus is usually integrated in one equipment with the phaco emulsification cataract removal apparatus, so the equipment is bodily large, design complex, cost high and operation inconvenient; in addition, the pneumatic apparatus operating frequency is within the audio range, so it is noisy and has high needle tip moving displacement.

In the prior arts, there are many ultrasonic phaco emulsification apparatus, but no practically useful ultrasonic vitrectomy apparatus. There is no still appropriate ultrasonic vitrectomy needle, or related ultrasonic apparatus or hand piece to safely drive a long slim needle with a through center bore, so that it is able to reach a certain ultrasonic magnitude and depth into the vitreous body for liquefying and crushing it.

BRIEF SUMMARY

Provided is an ultrasonic vitrectomy needle, to make the vitreous body removal by ultrasonic technology a practical reality. By applying the advantages of ultrasonic vibration of noise-free, micro-displacement, fluid-repulsion and viscosity-reduction, a practically usable ultrasonic vitrectomy needle is provided, and the surgical safety is improved.

Provided is an ultrasonic vitrectomy needle, including: a connector and a connected inner needle, the characteristic is: outside of the inner needle there is a sheath tube; the sheath tube is slightly longer at the distal end than the inner needle; the sheath distal end is blind non-sharp smooth surface, but there is an open port at the distal end side for aspirating vitreous body.

At the fastening portion distal end, surrounding the inner needle, there is a counter bore; the sheath tube proximal end inserted in the counter bore, and the contacting area between the sheath and fastening portion is sealed/adhered with plastic sealant/adhesive. The distal end counter bore is used to receive, adjust and fix the sheath position.

There is gap between the sheath tube inner wall and the inner tube outer wall.

In the connector body there is a center bore running through the body; the center bore has the matching shape as to the inner needle, used to receiving the inner needle, and the center axis of the connector coincides with that of the inner needle.

Outside sheath tube distal end is blind with a flat surface, or a convex round surface. Of course, known by the skills in this field, other non-sharp smooth end surfaces can used to instead.

The connector includes a fastening portion, a threaded portion for connecting to a hand piece, and a tapered portion at the proximal end for tightening the inner needle. The fastening portion is a feature used for wrench gripping, having matching shape and size to the wrench tool. The threaded portion is outer thread located on distal end outside of the connector body. The tapered portion is located at the proximal end of the threaded portion, and the tapered portion is adapted to the inner lumen in the ultrasonic hand piece.

On the tapered portion, there is at least one slit used for tightening the inner needle.

The vitrectomy needle by the connector is connected to the hand piece distal end, and the hand piece through an electric cable is connected to the ultrasonic emulsification apparatus.

In the distal end of the hand piece is an inner thread that matching the threaded portion on the connector.

In the proximal end of the inner thread in the distal end of the hand piece is a tapered surface that matches the taper portion on the connector, which helps tightening the slit(s) on the tapered portion, to improve the security of the inner needle.

Comparing to the prior art of pneumatic driven vitrectomy apparatus, the ultrasonic vitrectomy apparatus from this invention possesses advantages such as minimized-noise and micro-displacement, and it can be easily integrated to the currently commonly used phaco emulsification system. The benefits of this invention may include:

(1) As it is concerned as the long slim center bore needle for the ultrasonic surgical system, this invention makes the ultrasonic vitrectomy a practical reality. The ultrasonic vibration inherent advantages of minimized-noise, micro-displacement fluid-repulsion and viscosity-reduction improved the safety of the surgery.

(2) The design of the outer sheath for the ultrasonic vitrectomy needle: the distal end is a blind non-sharp smooth surface, but at the side of the distal end where is longer than the inner needle has a side port, which is used to aspirating the vitreous body. The smooth distal end prevents the delicate retina from inner needle ultrasonic vibration or cavitation causing damage, while the side port allows the inflow of the vitreous body for ultrasonic crashing. It solved the problem with the prior art that the sharp distal tip at the ultrasonic needle easily piercing the unintended tissues, thus reduced the risk and improve the safety of the surgery.

(3) The integration of the ultrasonic vitrectomy and the ultrasonic cataract emulsification greatly simplified the complicity of the apparatus of prior art, thus provides ease and cuts the cost for ophthalmic surgeries.

DETAILED DESCRIPTION

Figure 1:
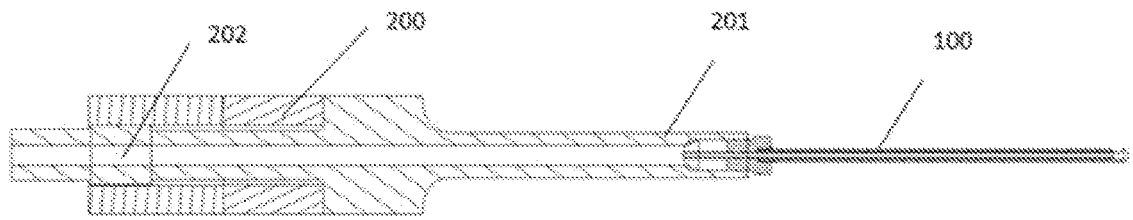
FIG. 1 is an illustration of an embodiment illustrates the connecting structure between the ultrasonic vitrectomy needle and the hand piece distal end.
Figure 2:
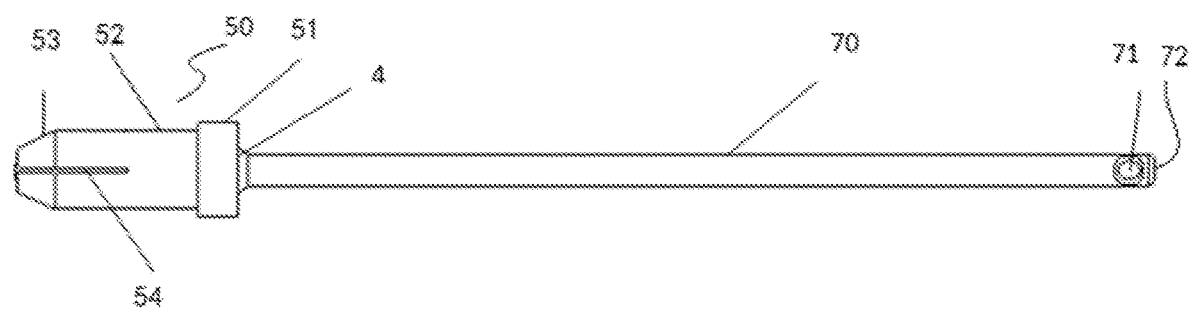
FIG. 2 is an illustration of an embodiment, side view of the ultrasonic vitrectomy needle.
Figure 3:
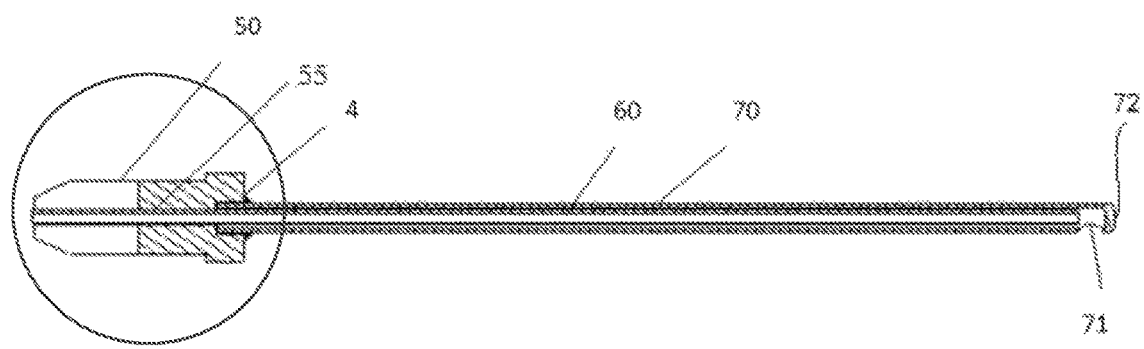
FIG. 3 is an illustration of an embodiment, cross section view of the ultrasonic vitrectomy needle.

Based on the illustrative Figures and the embodiments, this invention is described in detail below.

As illustrated in FIG. 2-FIG. 4, FIGS. 5A, 5B, and 5C, the ultrasonic vitrectomy needle comprises the connector 50 and with which the connected inner needle tube 60. In the connector 50 there is along the center axis a running through center bore 55, which has the shape matching the inner tube 60 for accommodating the inner tube 60. Part of the inner tube 60 is inserted in the center bore 55, and the axis of the inner tube 60 coincides with the axis of the center bore 55; the other part of the inner tube 60 is outside of the connector body 50 and extends to the distal end; outside the connector body 50, the extended portion of the inner tube 60 is covered by an outer sheath 70; the length of the sheath is slightly longer at the distal end than the inner tube 60, and the distal end 72 is a blind non-sharp smooth surface, while there is a port 71 at the side of the distal end where is the longer portion than the inner tube 60. The side port 71 is used for aspirating the vitreous body.

In a preferable embodiment, the distal end 72 of the outer sheath 70 is a convex round surface. Of course it can be other no-sharp smooth surfaces known to the skills in the field.

In a preferable embodiment, the size of the center bore 55 is lightly bigger than the size of the inner needle 60 for receiving the needle 60; the shape of the center bore 55, matches the shape of the inner needle 60, such as can be polygons, and the axis of the inner needle coincides with the axis of the connector.

Figure 4:
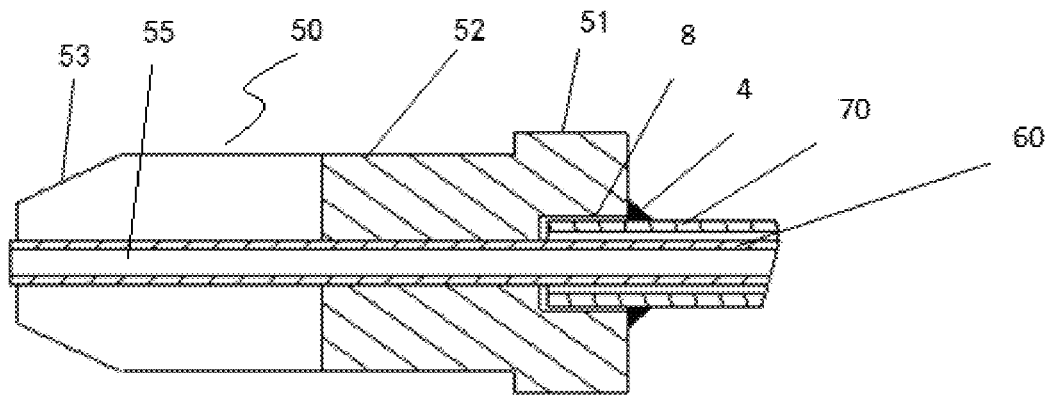
FIG. 4 is a detailed view of FIG. 3 at the connecting area.
Figure 5A:
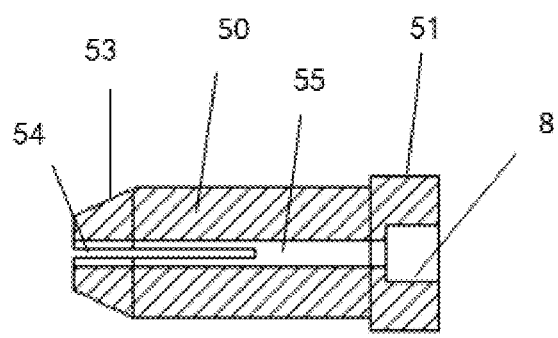
FIG. 5A is the cross section view of the connector.
Figure 5B:
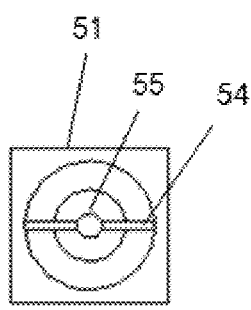
FIG. 5B is the side view of FIG. 4.
Figure 5C:
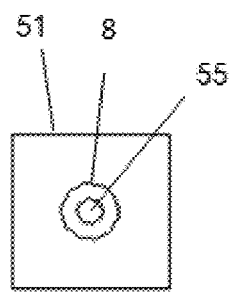
FIG. 5C is the side view of the connector from the fastening portion side.

Illustrated in FIG. 4 and FIG. 5A is an embodiment of the connector 50, including the fastening portion 51, the nearby threaded portion 52 for connecting to the ultrasonic hand piece, and the tapered portion 53 at the proximal end for tightening the inner needle. The fastening portion 51 is gripping surfaces for a wrench tool with the adapting shape and size; the threaded portion 52 is the outer thread located on the outside surface of the connector 50; the tapered portion 53 is located at the proximal end of the threaded portion 52, and it has the tapered shape adapting to the ultrasonic hand piece inner lumen; there is at least one evenly distributed slit 54 on the tapered portion 53 for tightening the inner needle 60.

At the distal end face of the fastening portion 51, surrounding the inner needle 60, is a counter bore 8 (FIG. 4,5); the proximal end of the sheath tube 70 is inserted in the counter bore 8, and the contacting area between the sheath 70 and the fastening portion 51 is sealed/adhered by plastic sealant/adhesive 4. The counter bore 8 on the fastening portion 51 distal end is used for receiving, adjusting and poisoning the center position of the sheath 70. There is a gap between the sheath 70 and the inner needle 60, so during working, only the inner needle 60 has ultrasonic vibration, while the outer sheath 70 does not vibrate, nor reduce the output of the ultrasonic vibration.

When applying the ultrasonic vitrectomy needle, the threaded portion 52 of the connector 50 is mated to the inner thread at the distal end of the hand piece, i.e., through the thread mating, the connector 50 is screwed into the ultrasonic hand piece distal end, the guiding tapered portion 53 is adapted to the tapered surface in the hand piece. Meanwhile, the slit 54 is partially closed due to the squeezing, and the tapered surfaces of the tapered portion closely touched the inner surface of the hand piece. Due to the deformation of the slit 54, the diameter of the center bore 55 is also changed, so the inner needle is rigidly coupled to the connector 50, and then to the hand piece distal end, thus the ultrasonic vibration is effectively propagated to the ultrasonic surgical tool distal tip.

When applying the ultrasonic vitrectomy apparatus, as shown in FIG. 1, through the connector 50, the ultrasonic vitrectomy needle 100 is connected to the ultrasonic hand piece 200 distal end, the inner needle 60 is tightened, and the ultrasonic hand piece is connected to the ultrasonic phaco emulsification equipment through the electric cable. When power is turned on, the ultrasonic vibration can be effectively propagated from the hand piece front rod 201 to the inner needle 60 distal tip. There is a gap between the outer sheath inner wall and the inner needle 60 outer wall, thus, when working, only the inner needle has ultrasonic vibration, while the outer sheath kept still from ultrasonic vibration. When the vitreous body resulted from the vacuum and the inner ocular pressure, through the outer sheath 70 side port 71 flows into the sheath, by the effects of the ultrasonic fragmenting, liquefying and viscosity reducing from the inner needle 60 distal tip, the vitreous body can be aspirated out through the inner needle 60 lumen and the hand piece center aspiration lumen 202, even under a lower aspiration pressure.

It should be understood, although the above description is based on the embodiments, each embodiment is not limited to one independent technical solution, for example, the inner needle 60 may be made of medial grade metals, or of medical grade plastics; the length of the inner needle 60 should be designed in a certain range not to reduce the ultrasonic vibration. In addition, due to the desire of small incision for the vitrectomy procedure, the inner needle is required within a small diameter range, usually is smaller than 500 μm, preferably 200-500 μm. The inner needle can be made of metal, plastic or resin etc. preferably of metal.

Disclosed is an ultrasonic vitrectomy apparatus, which includes the integrated ultrasonic emulsification apparatus, the ultrasonic hand piece and afore described ultrasonic vitrectomy needle. Through the outer threaded portion 51 on the connector 50 mating to the inner thread of the hand piece distal end, the ultrasonic vitrectomy needle is connected to the hand piece; at the proximal end of the inner thread on the hand piece is a tapered surface, which matches the tapered portion of the connector, in order to further closing the slit and tightening the inner needle; the ultrasonic hand piece is connected to the ultrasonic phaco emulsification apparatus.

The above illustrated and described the basic principle, major characteristics and the benefits of this invention. It should be understood by the skills in this field, this invention is not limited by the above mentioned embodiments. The above embodiments and the descriptions were only used to illustrate the principle of the invention. Not apart from the spirit and the protection of the invention, there are still other alternatives and improvements, all of which shall fall in the protection of the invention. The protection range are determined by the claims and equivalent objects.

The invention claimed is:

1. An ultrasonic vitrectomy needle, comprising:
   a connector having a distal end and a proximal end; and
   an inner needle, the inner needle located in an outer sheath, the inner needle and the outer sheath including distal ends and proximal ends;
   wherein the inner needle and the outer sheath are received by the connector at the distal end of the connector, wherein the proximal end of the inner needle extends to the proximal end of the connector and is received by at least one slit at the proximal end of the connector; and
   wherein the distal end of the outer sheath extends beyond the distal end of the inner needle;
   wherein the distal end of the outer sheath is blind, the outer sheath including an opening at a side near the distal end for aspirating a vitreous body.

2. The ultrasonic vitrectomy needle according to claim 1, wherein the distal end of the connector has a counter bore, wherein the proximal end of the outer sheath is inserted in the counter bore, and wherein a sealing material is provided at a contacting area between the distal end of the connector and the proximal end of the outer sheath.

3. The ultrasonic vitrectomy needle according to claim 1, wherein there is a gap between an inner surface of the outer sheath and an outer surface of the inner needle.

4. The ultrasonic vitrectomy needle according to claim 1, wherein the connector includes a central bore having a central axis and extending through the connector, wherein a shape of the central bore corresponds to a shape of the inner needle and is configured to receive the inner needle, wherein the center axis of the connector coincides with a central axis of the inner needle.

5. The ultrasonic vitrectomy needle according to claim 1, wherein the distal end of the outer sheath is blind with a flat smooth surface or with a convex smooth surface.

6. The ultrasonic vitrectomy needle according to claim 1, wherein the distal end of the connector includes a fastening portion, and the proximal end of the connector includes a tapered portion, wherein the connector includes a threaded portion between the fastening portion and the tapered portion.

7. The ultrasonic vitrectomy needle according to claim 1, wherein the at least one slit secures the proximal end of the inner needle to the connector.

8. An ultrasonic vitrectomy apparatus, comprising:
   integrated ultrasonic phaco emulsification equipment,
   a phaco hand piece, and
   an ultrasonic vitrectomy needle according to claim 1,
   wherein the connector of the ultrasonic vitrectomy needle is coupled to a distal end of the phaco hand piece, and the phaco hand piece is plugged to the ultrasonic phaco emulsification equipment.

9. The ultrasonic vitrectomy apparatus according to claim 8, wherein the distal end of the phaco hand piece includes inner threads that mate with outer threads of the connector, wherein a proximal end of the inner threads of the phaco hand piece has a tapered surface that corresponds to a tapered portion of the connector.

10. The ultrasonic vitrectomy needle according to claim 1, wherein the distal end of the connector has a counter bore, wherein the proximal end of the outer sheath is in the counter bore.

* * * * *